United States Patent
Terry et al.

(12)

(10) Patent No.: US 6,235,788 B1
(45) Date of Patent: May 22, 2001

(54) METHOD FOR TREATING PRE-MALIGNANT BASAL AND SQUAMOUS CELL LESIONS OF THE EPITHELIUM

(76) Inventors: James M. Terry, 221 Espanola Way; Richard R. Rathmann, 800 S. Harbor City Blvd., both of Melbourne, FL (US) 32901

(*) Notice: Subject to any disclaimer, the term of this patent is extended or adjusted under 35 U.S.C. 154(b) by 0 days.

(21) Appl. No.: 09/399,322

(22) Filed: Sep. 20, 1999

Related U.S. Application Data

(60) Provisional application No. 60/101,114, filed on Sep. 21, 1998.

(51) Int. Cl.[7] .................. A61K 31/16; A61K 47/00; A61K 35/78; A61K 39/385
(52) U.S. Cl. ................ 514/627; 514/783; 424/195.1
(58) Field of Search .................................. 514/627, 783; 424/195.1

(56) References Cited

PUBLICATIONS

Jang et al., J. Korean Med. Sci., 6(1), 31–6 Abstract Only, 1991.*
Park et al., 114(1,2), 183–184 Abstract Only, 1997.*
Ellison et al., J. Clin. Oncol., 15(8), 2974–2980 Abstract Only, 1991.*

* cited by examiner

*Primary Examiner*—Jerome D. Goldberg
(74) *Attorney, Agent, or Firm*—M K Silverman; Li Yi

(57) ABSTRACT

A new use of the botanical substance Capsaicin entails application of Capsaicin to pre-malignant basal and squamous cell lesions of the epithelium. Advantageous treatment, including atrophication and de-coloration of such lesions is accomplished. The substance, which is applied topically, is employed in a potency, or concentration, of about 0.010% to 0.200% (w/w). Capsaicin in the same potency can also be employed in a base of aloe vera.

4 Claims, No Drawings

METHOD FOR TREATING PRE-MALIGNANT BASAL AND SQUAMOUS CELL LESIONS OF THE EPITHELIUM

REFERENCE TO RELATED APPLICATION

Parts of this application correspond in subject matter to that of Provisional Application Serial No. 60/101,114 filed Sep. 21, 1998.

BACKGROUND OF THE INVENTION

The botanical substance Capsaicin, a derivative of Cayenne pepper and of other types of peppers, chilies and the like grow, in different areas of the world. As such, Capsaicin is a naturally occurring substance derived from plants of the Solanaceae family, and having a chemical name of trans 8, methyl-N-vanillyl 6-nonemamide. The same, in a chemical notation, corresponding to $C_{18}H_{27}NO_3$. Capsaicin is a white crystalline power having a molecular weight of 305.4. It is substantially insoluble in water, however. is highly soluble in alcohol, ether, and chloroform.

While to the general public, Capsaicin is simply the chemical name for various forms of cayenne peppers, the biomedical community has recognized that Capsaicin provides a mechanism of action which is of value in the treatment of rheumatoid arthritis, osteoarthritis, certain forms of neuralgias and diabetic neurophepy. Commercial forms of Capsaicin exist as arthritis creams which are applied topically to joints where painful arthritis exists.

Park, et al, in *Cancer Letters* (1977), 114 (1,2), 183–184, AN 1997:223231 CAPLUS). Dm 126:260335, teach use of Capsaicin, in rats, as a prophylaxis, that is, as a preventative measure to lower the incidence of skin cancer, not to treat an existing lesion, that is, a lesion that has already come into existence as do the within inventors. In Parks, Capsaicin is applied entirely to nonnal (albeit non-human) epithelial tissue.

To the knowledge of the inventors, no other bio-medical applications of the botanical substance Capsaicin are known in the art. The present invention therefore relates to a dermatological use of Capsaicin having particular application in the treatment of pre-malignant tumors, this as is more fully set forth below.

SUMMARY OF THE INVENTION

The instant invention relates to a method of treating pre-malignant lesions, consisting of application of Capsaicin to pre-malignant lesions of the epithelium, this pre-malignant including basal and squamous cell lesions. Thereby, advantageous treatment, including atrophication and decoloration of such lesions, is accomplished. The Capsaicin, which is applied topically, is employed in a potency, or concentrations of at least 0.010% (w/w), with an average potency, or concentrations of 0.035% (w/w). Aloe vera may be employed in combination with the Capsaicin.

It is an object of the present invention to provide a new use of the botanical substance Capsaicin having particular reference to treatment of lesions of the skin to prevent them from becoming malignant.

It is another object to provide a biomedical use of Capsaicin by which topical tumors, scales and lesions can be substantially dissipated before their transformation into basal or squamous cell malignancies.

It is a further object to provide a means of prevention of cancers of the skin.

The above and yet other objects and advantages of the present invention will become apparent from the hereinafter set forth Detailed Description of the Invention and claims appended herewith.

BRIEF DESCRIPTION OF THE DRAWINGS

There are no drawings in this application.

DETAILED DESCRIPTION OF THE INVENTION

Certain scale-like lesions of the skin (clinically termed heaped-up particles of the epithelium) have been identified as precursors of basal and squamous cell malignancies of the skin. The same comprise brown skin spots which are most common among older persons, particularly in Sunbelt areas of the country such as Florida, Texas, Arizona and California.

The within inventors have discovered, through observations of the action of their proprietary form of Capsaicin in the treatment of arthritis, that decoloration, atrophication and, in some cases, complete disappearance of such brown spots upon the skin is accomplished through the topical application of Capsaicin in potencies, or concentrations in a range of 0.010% to 0.200% (w/w), with an average potency, or concentrations of 0.035% (w/w).

EXAMPLE 1

Capsicum was initially tested upon persons having pre-malignant basal or squamous cell lesions at joints and other areas of the body subject to arthritis. Thereby, the inventors sought out, as an initial test group, older individuals in Florida, Arizona and California, having pre-malignant scaling of the skin in parts of the body, typically joints, in which one or more of the above-noted Capsaicin arthritis products would otherwise be indicated for use. In this test, the inventors discovered that pre-malignant cell lesions in the area of joints being so treated for arthritis would, over a period of days of treatment, became lighter in color, atrophy, and in many cases disappear completely.

EXAMPLE 2

After having completed the above test group, the inventors proceeded to use of Capsaicin upon persons not having any arthritis problems and to treat such persons upon parts of the body unrelated to joints. In particular, the inventors applied a roll-on stick form of Capsaicin to such areas as bald heads and arms of older persons where such premalignant cell lesions are common. In such testing, the same marked results were obtained as in the group of Example 1.

From such testing, It is believed that an appropriate range of concentration of Capsaicin is between 0.010% and 0.200% (w/w), with a preferred range being that of 0.025% to 0.099% (w/w).

EXAMPLE 3

A Caucasian male in Indian Harbor Beach, Florida, experimentally utilized Capsaicin, in said preferred range, in January 1997, for the treatment of pre-malignant lesions, and found a complete clearing thereof within a period of weeks, following daily usage thereof.

EXAMPLE 4

A Caucasian male in Downey, California, experimentally utilized Capsaicin, in said preferred range, October 1997, for the treatment of pre-malignant lesions, and found a complete clearing thereof within a period of weeks, following daily usage thereof.

EXAMPLE 5

A Caucasian female in West Covina, California experimentally utilized Capsaicin, in said preferred range, in July 1998, for the treatment of pre-malignant lesions, and found a complete clearing thereof within a period of weeks, following daily usage thereof.

As is well known in clinical dermatology, the best treatment for any type of basal or squamas cell carcinoma is to prevent it from becoming malignant in the first place. Since basal and squamous cell carcinomas represent one of the few forms of cancer which are readily observable, the same are ideal candidates for preventative treatment, and the present invention is therefore to be viewed as a contribution in the area of preventative medicine, in that Capsaicin can, without risk, be liberally applied to such pre-malignant lesions at their earliest appearance.

EXAMPLE 6

A Caucasian male in Concord, New Hampshire, experimentally utilized the above Capsaicin formulation, in a base of aloe vera, for the treatment of pre-malignant lesions, and found a complete clearing thereof within a period of weeks, following daily usage thereof.

EXAMPLE 7

A Caucasian male in Carbondale, Illinois, experimentally utilized the above Capsaicin formulation, in a base of aloe vera, for the treatment of pre-malignant lesions, and found a complete clearing thereof within a period of weeks, following daily usage thereof.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

What is claimed is:

1. A method for treating pre-malignant basal and squamous cell lesions of the epithelium comprising the step of:

applying an enhanced effective amount of Capsaicin in a concentration from about 0.010% to about 0.200% (w/w) in a base of aloe vera topically on an area of said lesion, whereby advantageous treatment, including atrophication and de-coloration of such lesions, is thereby achieved.

2. The method as recited in claim 1, wherein applying Capsaicin in a base of aloe vera topically can be by dabbing.

3. The method as recited in claim 1, wherein applying Capsaicin in a base of aloe vera topically can be by using a roll-on stick, or topical cream.

4. The method as recited in claim 1, wherein said Capsaicin is in a concentration from about 0.025% to about 0.099% (w/w).

* * * * *